United States Patent [19]
Durante et al.

[11] Patent Number: 5,962,752
[45] Date of Patent: Oct. 5, 1999

[54] LEACHED ALUMINA VANADYL CATALYSTS FOR HYDROXYLATION OF AROMATICS USING MOLECULAR OXYGEN AS THE TERMINAL OXIDANT WITHOUT COREDUCTANT

[75] Inventors: Vincent A. Durante, West Chester; Tilak P. Wijesekera, Glen Mills; Swati Karmakar, Malvern, all of Pa.

[73] Assignee: Sun Company, Inc., Philadelphia, Pa.

[21] Appl. No.: 08/903,824

[22] Filed: Jul. 31, 1997

[51] Int. Cl.⁶ .................................................. C07C 37/00
[52] U.S. Cl. ............................................ 568/802; 568/741
[58] Field of Search ...................... 568/802, 741

[56] References Cited

U.S. PATENT DOCUMENTS

| | | | |
|---|---|---|---|
| 1,595,299 | 8/1926 | Hale | 568/802 |
| 2,456,597 | 12/1948 | Schlesman | 568/802 |
| 4,338,471 | 7/1982 | Umemura | 568/802 |
| 4,515,983 | 5/1985 | Goel | 568/802 |
| 4,982,015 | 1/1991 | Chao et al. | |
| 4,992,600 | 2/1991 | Chao et al. | |
| 5,110,995 | 5/1992 | Kharitinov et al. | |
| 5,233,097 | 8/1993 | Nemeth et al. | |
| 5,426,245 | 6/1995 | Hamada | 568/802 |

FOREIGN PATENT DOCUMENTS

| | | |
|---|---|---|
| 02115138 | 4/1990 | Japan . |
| 03236338 | 10/1991 | Japan . |
| 07238042 | 9/1995 | Japan . |

OTHER PUBLICATIONS

Iwamoto, J. Phys. Chem., vol. 87, pp. 903–905, 1983.

Kitano et. al., Bull. Chem. Soc. Japan. vol., 67, No. 10, pp. 2850–2855, (1994). "Gas phase Oxidation of Benzene to Phenol under the Simultaneous Feeding of Hydrogen and Oxygen. III. Catalyst Prepared from Cu(11) Phosphate".

Jintoku et. al., Chemistry Letters pp. 1687–1688, (1990) Chemistry Letters [The Chemistry Society of Japan] "Palladium Catalyzed Transformation of Benzene to Phenol with Molecular Oxygen".

Miyake et. al., Applied Catalysis A: General vol. 131, pp. 33–42, (1995). "Direct Synthesis of Phenol by Hydroxylation of Benzene with Oxygen and Hydrogen".

de Resende et. al., Preparation of Catalysts V1—Scientific Bases for the Preparation of Heterogeneous Catalysts, pp. 1050–1067, (1995). "Synthesis and Characterization of Titanium Oxide Monolayer".

Kodama et. al., Bull. Chem. Soc. Japan., vol. 68, pp. 1627–1633, (1995). "Formation Equilibrium of a Cooper(11)–Binuclear Complex of a New Pyridyl–Containing Tetraoxo Octaaza Macrocyclic Ligand and Its Polarograhic Reduction behavior".

Lam et. al. J. Chem. Soc., Chem. Commun., pp. 2439–2440, (1994). "Synthesis of Novel Dinickel(11) and Nickel(11)–Copper(11)Bimetallic Complex derived from and Acyclic Dinucleating Schiff Base–Pyridine Ligand".

*Primary Examiner*—Michael L. Shippen

[57] ABSTRACT

A process is disclosed for the catalytic hydroxylation of aromatic hydrocarbons which comprises contacting aromatic feedstock with oxidant comprising molecular oxygen, under suitable reaction conditions, in the presence of a catalyst comprising vanadyl ($V^{IV}$) on an alumina support, preferably on leached alumina. The process is particularly suited, for example, to the one-step conversion of benzene to phenol.

13 Claims, No Drawings

LEACHED ALUMINA VANADYL CATALYSTS FOR HYDROXYLATION OF AROMATICS USING MOLECULAR OXYGEN AS THE TERMINAL OXIDANT WITHOUT COREDUCTANT

FIELD OF THE INVENTION

This invention pertains to the hydroxylation of aromatic hydrocarbons, for example, the hydroxylation of benzene to phenol, using molecular oxygen as terminal oxidant and to catalysts useful in such processes.

BACKGROUND OF THE INVENTION

Phenol is a valuable commodity intermediate chemical which is among the top 10 organic chemical monomers produced in the US. Principal applications for phenol are as an intermediate to bisphenol A (used in turn to make polycarbonates); as a component in phenol-aldehyde resins, coatings, and adhesives; as a precursor to caprolactam (precursor to Nylon-6), detergents, antioxidants, and to a number of other chemicals which are used in diverse applications. Other hydroxylated aromatics are also of commercial importance. For example, cresols are used largely to manufacture herbicides and insecticides and antioxidants; 2,6-xylenol is the starting material for polyphenylene oxide, a thermoplastic with high heat and chemical resistance and excellent electrical properties developed by General Electric Co. Salicylic acid, dihydroxybenzenes including resorcinol, pyrocatechol, and hydroquinone are also derivatives.

Starting from benzene, the dominant current route to phenol is the "cumene peroxidation process" which requires multiple steps and produces coproduct acetone, markets for which are expected to grow much more slowly than those for phenol. This route also consumes propylene for which there are alternative applications which often produce greater economic return. In this process, benzene is first alkylated to cumene with propylene. Then in a second step, cumene is oxidized with air to the hydroperoxide which, in turn, is subsequently decomposed in the presence of acid to a 1:1 mixture of acetone and phenol:

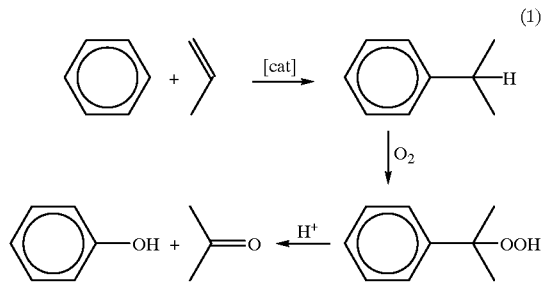

(1)

Another route to phenol which accounts for less than 2% of industrial capacity in the US, is the "toluene oxidation route". In this route, toluene, not benzene, is catalytically oxidized to benzoic acid. In a second step, the benzoic acid is catalytically oxidatively decarboxylated to a 1:1 ratio of phenol and carbon dioxide, the latter being another usually undesired "greenhouse gas" byproduct. In addition to producing a low value byproduct, this route is also capital intensive due to the need for a complex product and catalyst recovery scheme:

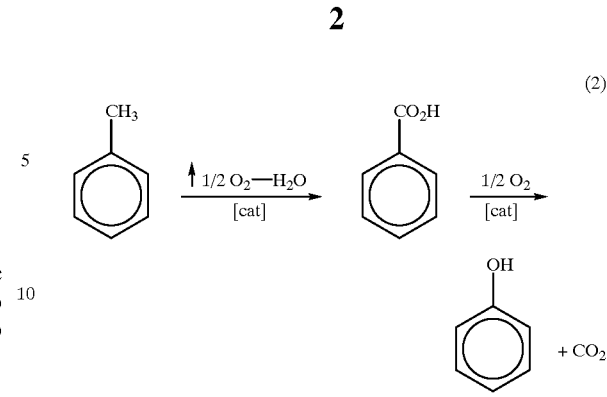

(2)

Still other obsolete routes to phenol through halobenzene intermediates are known in the art, but these are no longer practiced commercially. Cresols and xylenols can be prepared by methylation of phenol with methanol in gas or liquid phase processes.

A commercially viable process for the direct, one-step oxidation of benzene to phenol (equation 3) would not only be simpler than dominant routes now practiced, but would also enable phenol or its derivatives to be marketed unencumbered by the need to find outlets for acetone or carbon dioxide coproducts and, furthermore, would consume no propene.

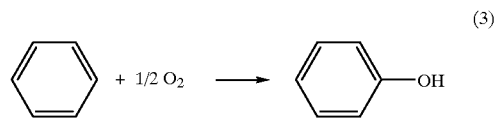

(3)

A number of workers have produced phenol from benzene over the years using molecular oxygen (or air) as the oxidant over a variety of catalysts, usually at high temperature. Unfortunately, ineluctable deep oxidations of benzene generally occur at the needed temperatures which lead to ring cleavage products such as carbon dioxide, carboxylic acids or anhydrides such as maleic anhydride, in toto resulting in poor selectivity from hydroxylation.

More selective hydroxylation of benzene without ring cleavage can be achieved at reasonable space-time yields using other oxidants such as hydrogen peroxide, nitrous oxide, tert-butyl or cumyl hydroperoxide, but these oxidants are up to 50 times more costly per oxygen equivalent than is dioxygen. In still other catalytic processes, molecular oxygen serves as the oxidant, but a stoichiometric co-reactant such as carbon monoxide or hydrogen must be co-fed to the catalyst. This practice not only augments the process costs to prohibitive levels, but also represents an engineering challenge to overcome heightened possibilities for uncontrolled oxidations or explosions. Certain of these processes are patented or described in publications; see, for example, K.-H. Chao et al., U.S. Pat. Nos. 4,982,015 and 4,992,600; Nemeth et al., U.S. Pat. No. 5,233,097; Kharitinov et al., U.S. Pat. No. 5,110,995; Sasaki et al., Bull. Chem. Soc. Jpn., 2850 (1994); Jintoku et al., Chem.Lett. 1687 (1990); Miyake et al., Appl. Cat. A, 131, 33 (1995); A. Matsudo et al., Jap. Pat. No. J03236338-A (1991).

In contrast, there is no previously known route to produce phenol from benzene which uses molecular oxygen as the sole oxidant with no requirement for a coreductant that yields phenol with sufficient selectivity and at sufficient space-time-yield so as to be commercially viable. The present invention provides such a process using $O_2$ with low severity reaction conditions and good selectivity. An advantage of the present invention is to provide a method for the hydroxylation of aromatic compounds which does not require the added reagent and engineering costs and operational risks associated with the use of coreductants such as hydrogen or carbon monoxide. A further advantage of the present invention is to provide a method for the hydroxylation of aromatics which can use molecular oxygen as the terminal oxidant thereby avoiding the need for more expensive oxidants.

SUMMARY OF THE INVENTION

The present invention comprises a process for catalytic hydroxylation of aromatic hydrocarbons which comprising contacting aromatic feedstock with oxidant comprising molecular oxygen, under suitable reaction conditions, in the presence of a catalyst comprising vanadyl ($V^{IV}$) on an alumina support. Preferably, the support comprises leached alumina. The process is particularly suited, for example, to the one-step conversion of benzene to phenol. According to the process of the invention, the direct hydroxylation of aromatics can be catalyzed using oxygen, but without catalytic promoters and without coreductants.

DETAILED DESCRIPTION OF THE INVENTION

The present invention comprises a process for catalytic hydroxylation of aromatic hydrocarbons which comprising contacting aromatic feedstock with oxidant comprising molecular oxygen, under suitable reaction conditions, in the presence of a catalyst comprising vanadyl ($V^{IV}$) on an alumina support. Preferably, the support comprises leached alumina. Suitable catalysts comprise vanadyl sulfate or vanadyl oxalate on leached leached alumina. The process is particularly suited, for example, to the one-step conversion of benzene to phenol. According to the process of the invention, the direct hydroxylation of aromatics can be catalyzed using oxygen, but without catalytic promoters and without coreductants.

The Process

The process of the present invention pertains to the hydroxylation of aromatic feedstocks without the introduction of stoichiometric co-reductant to the system; e.g., without $H_2$ added to the $O_2$ oxidant system. This does not exclude the presence of initiators or modifiers of the catalyst which may be present in situ prior to steady-state operations; the presence of such initiators or modifiers is within the scope of the present invention.

Under some reaction conditions that are suitable for the ring hydroxylation to occur, side chain oxidation may also occur competitively. Side chain oxidation would consume a portion of the oxidant in the reactor; nevertheless, such reactions are within the scope of the present invention, provided that ring hydroxylation also takes place. More usually, one would prefer to minimize selectivity for side chain oxidation, and in such case, process conditions and/or catalyst components could be selected to mitigate the degree of side chain oxidations.

The process can be conducted over a range of reaction temperatures and pressures. The temperature may be in the range from 70 to 400° C.; preferably 150 to 280° C.; and more preferably 180 to 240° C. The pressure may be in the range from 0 to 6000 psig; preferably 100 to 2000 psig; and more preferably 300 to 900 psig. Preferably, the reaction is carried out under conditions outside the explosive range for the temperature, pressure and oxygen concentrations employed.

Suitable oxygen concentrations would comprise from 1 to 95 volume percent (vol. %) of oxygen in the gas phase at the temperature and pressure of the reaction; preferably the oxygen concentration is 5 to 50 vol. %; more preferably, 7 to 15 vol. %. To avoid explosive concentrations of oxygen, particularly in a continuous reactor, it may be desirable to pre-mix oxygen or air and steam to dilute the oxygen prior to addition of the aromatic feedstock. Suitable weight ratios of aromatic feedstock to water in the reaction process are 2000:1 to 0.2:1; preferably 1700:1 to 50:1; more preferably 1600:1 to 100:1. The oxidant may be molecular oxygen or air or other mixtures comprising $O_2$. Other oxidants, such as hydrogen peroxide, nitrous oxide and organic hydroperoxides, may also be used in the process of the present invention when carried out in liquid phase and under narrower process conditions. The choice of solvent should be such that it does not cause the vanadyl compound to be dissolved off the support.

The process can be conducted in different reactor configurations with either liquid phase, vapor phase, multiple liquid phase, or mixed liquid and gaseous phases of the aromatic feedstock depending on the operating parameters. Likewise, a variety of reactor types could be employed to advantage, the focus of the invention being primarily in the use of the catalysts described herein within the temperature, pressure, and oxygen concentration ranges specified herein. Suitable reactor types include, but are not limited to, packed beds, fluidized beds, slurry phase reactors, stirred tank reactors, and reactive distillation columns. Preferably, an isothermal reactor is used to carry out the process of the invention.

The Feedstocks

The aromatic feedstocks suitable for use in the process of the present invention may comprises unsubstituted aromatics, such as benzene and naphthalene, and compounds in which the aromatic nucleus is substituted with one or more substituents. Suitable substituted aromatic compounds may comprise aromatics substituted with one or more of the following substituents: lower alkyl groups such as methyl, ethyl, propyl, butyl; lower alkoxy groups such as methoxy, ethoxy, propoxy, etc.; halogen atoms such as chlorine, bromine, fluorine, iodine; amino and alkylamino groups; carboxyl, nitro, nitroso, sulfo, sulfone, sulfoxy groups. The foregoing list is not intended to be exhaustive and other substituents, alone or in combination with each other and/or the foregoing, may be incorporated into the feedstock ring systems so long as such substituents do not prevent ring oxidation.

The Catalysts

The catalysts useful in the process of the present invention consist of vanadyl ($V^{IV}$) on an alumina support. Preferably the support comprises leached alumina. The support serves to keep the vanadyl well dispersed. The vanadyl may be supplied to the catalyst in the form of vanadyl sulfate, vanadyl oxalate or other vanadyl-containing compounds. The catalyst may comprise about 0.2 to about 10 weight percent vanadium; preferably, about 1 to about 6 weight percent. The preparation of these catalysts is known in the art.

The catalysts useful in the process of the invention may be prepared as described in the Example below.

EXAMPLE

A catalyst according to the present invention was prepared by treating gamma alumina 1/16 inch extrudates with 1.0 F oxalic acid(aq) at 70° C. for 1–2 hours at 40% solids in aqueous slurry, followed by extensive washing with hot water and with aqueous ammonia, followed by air drying. The alumina was not calcined. An aqueous solution of vanadyl(IV)sulfate was prepared containing a large excess of vanadium. The alumina was slurried in this solution followed by washing with water and air drying. Based on vanadium in the wash water, it was estimated that the alumina retained enough vanadium to provide about 0.2 wt. % loading on a dry basis.

This catalyst was tested in an RM-CSTR reactor at a temperature of 178° C. and a pressure of 825 psig, using wet benzene, air and nitrogen feed. After 3 hours on stream, the standard time for comparison of tested catalysts, this catalyst generated 60% selectivity to phenol and a space-time-yield (STY) for phenol of 5.0 g phenol/kg catalyst/h. An earlier aliquot taken at 1 hour on-stream indicated that a selectivity of 92% and STY of 17 g phenol/kg cat/h had been produced.

The same batch of catalyst as above was unloaded from the RM-CSTR reactor and placed into a continuous downflow packed bed reactor along with a small amount of additional fresh catalyst and inert packing. Air at 43 mL NTP/min was passed into a premixing/heating chamber and then into the catalyst b ed along with water at 31.52 mg/min and benzene at 45.5 mg/min. The reactor was operated isothermally at 814 psig and 340° C. for several hours, followed by operation at 300° C. for four hours. Thereafter, a liquid aliquot was collected over a three hour period, and effluent gas was sampled periodically over that time period. A mole % benzene conversion of 4.0% was realized with a carbon atom selectivity of 13% to hydroxylated aromatic products (11% to phenol) and a space-time-yield of about 3.5 g phenol/kg catalyst/h to phenol. The major non-phenol product in the benzene layer was biphenyl which formed at 9% carbon atom selectivity. Carbon dioxide carbon atom selectivity was found to be 67%. The temperature was then dropped to 280° C., the pressure increased to about 930 psig, and the air flow rate lowered to 30 mL NTP/min with other process variables held as before. After an additional 2 hours on stream, benzene conversion was measured to be 1.8%, carbon selectivity to hydroxylated products was 34% (phenol >32 atomic percent), carbon selectivity was 7% to biphenyl, and 36% to $CO_2$. Acetic acid was found in the water layer. Space-time-yield to phenol was about 2 g phenol/kg cat/h.

What is claimed is:

1. A process for catalytic ring hydroxylation of aromatic hydrocarbons comprising contacting aromatic feedstock with oxidant comprising molecular oxygen under suitable reaction conditions in the presence of a catalyst comprising $V^{IV}$ on a leached alumina support.

2. The process of claim 1 wherein said catalyst comprises about 0.2 to about 10 weight percent vanadium.

3. The process of claim 2 wherein said catalyst comprises about 1 to about 6 weight percent vanadium.

4. The process of claim 1 wherein said reaction conditions comprise a temperature in a range from 70 to 400° C. and a pressure in a range from 0 to 6000 psig.

5. The process of claim 4 wherein said temperature is in a range from 150 to 280° C.

6. The process of claim 5 wherein said temperature is in a range from 180 to 240° C.

7. The process of claim 4 wherein said pressure is in a range from 100 to 2000 psig.

8. The process of claim 7 wherein said pressure is in a range from 300 to 900 psig.

9. The process of claim 1 wherein said aromatic feedstock comprises substituted aromatic compounds.

10. The process of claim 9 wherein said aromatic feedstock comprises benzene or naphthalene.

11. The process of claim 10 wherein said aromatic feedstock comprises benzene.

12. The process of claim 9 wherein said aromatic feedstock comprises substituted aromatic compounds comprising one or more substituents comprising alkyl groups, alkoxy groups, halogen atoms, amino groups, alkylamino groups, carboxyl groups, nitro groups, nitroso groups, sulfo groups, sulfone groups, or sulfoxy groups or combinations thereof.

13. The process of claim 1 wherein said aromatic feedstock comprises unsubstituted aromatic compounds.

\* \* \* \* \*